United States Patent [19]

Jørgensen et al.

[11] Patent Number: 5,700,914
[45] Date of Patent: Dec. 23, 1997

[54] PURIFICATION OF FACTOR VII

[75] Inventors: Tony Jørgensen, Ballerup; Anders Hjelholt Pedersen, Lyngby, both of Denmark

[73] Assignee: Novo Nordisk A/S, Bagsvaerd, Denmark

[21] Appl. No.: 446,671
[22] PCT Filed: Mar. 24, 1994
[86] PCT No.: PCT/DK94/00122
§ 371 Date: May 25, 1995
§ 102(e) Date: May 25, 1995
[87] PCT Pub. No.: WO94/22905
PCT Pub. Date: Oct. 13, 1994

[30] Foreign Application Priority Data

Mar. 31, 1993 [DK] Denmark .................................. 382/93

[51] Int. Cl.$^6$ .................. C07K 3/22; C07K 3/28; A61K 35/16
[52] U.S. Cl. .................. 530/412; 530/384; 530/416; 530/417
[58] Field of Search .................. 530/413, 384, 530/412, 416, 417

[56] References Cited

FOREIGN PATENT DOCUMENTS 0 363 126  4/1990  European Pat. Off. .

OTHER PUBLICATIONS

Radcliffe 1975 J. Biol Chem vol. 250(2) 388–395.
Broze et al 1980 J. Biol Chem vol. 255(2) 1242–1247.
Thim et al 1988 Biochemistry vol. 27: 7785–7793.
Pedersen et al (1991 Thrombosis & Haemostasis vol. 65(5):528–534.
Pusey et al 1985 Thromosis Res. vol. 39: 571–585.

*Primary Examiner*—Lila Feisee
*Assistant Examiner*—Julie E. Reeves
*Attorney, Agent, or Firm*—Steve T. Zelson, Esq.; Elias J. Lambiris, Esq.

[57] ABSTRACT

The present invention describes a method for controlled activation and degradation of FVII during purification whereby a solution of Factor VII is subjected to a number of chromatographic purification steps wherein $Zn^{++}$ is present in at least one of the purification steps.

The present invention also describes a method for controlled activation and degradation of FVII wherein a solution of FVII is applied to a number of anion exchange and immunoaffinity columns.

7 Claims, 3 Drawing Sheets

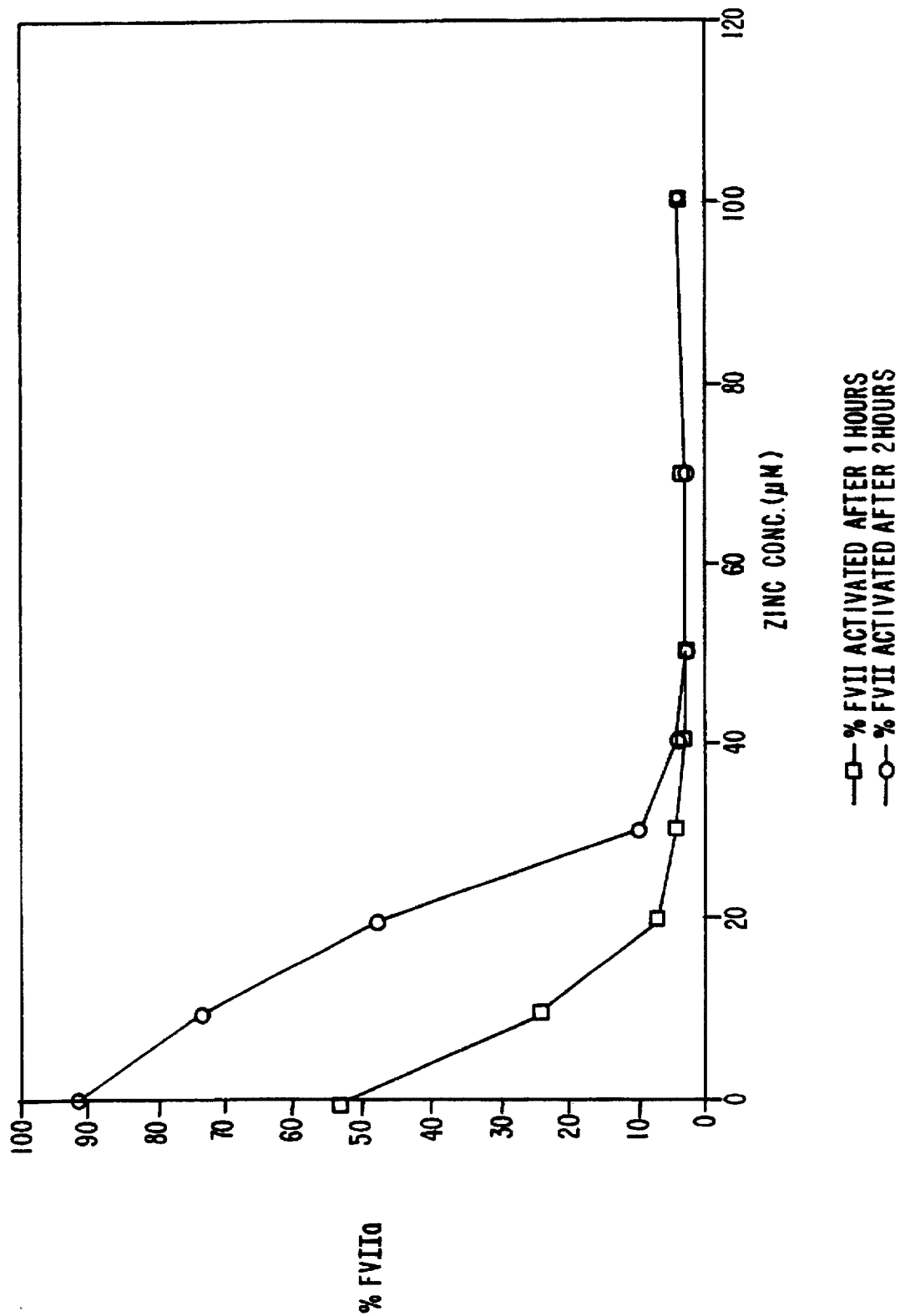

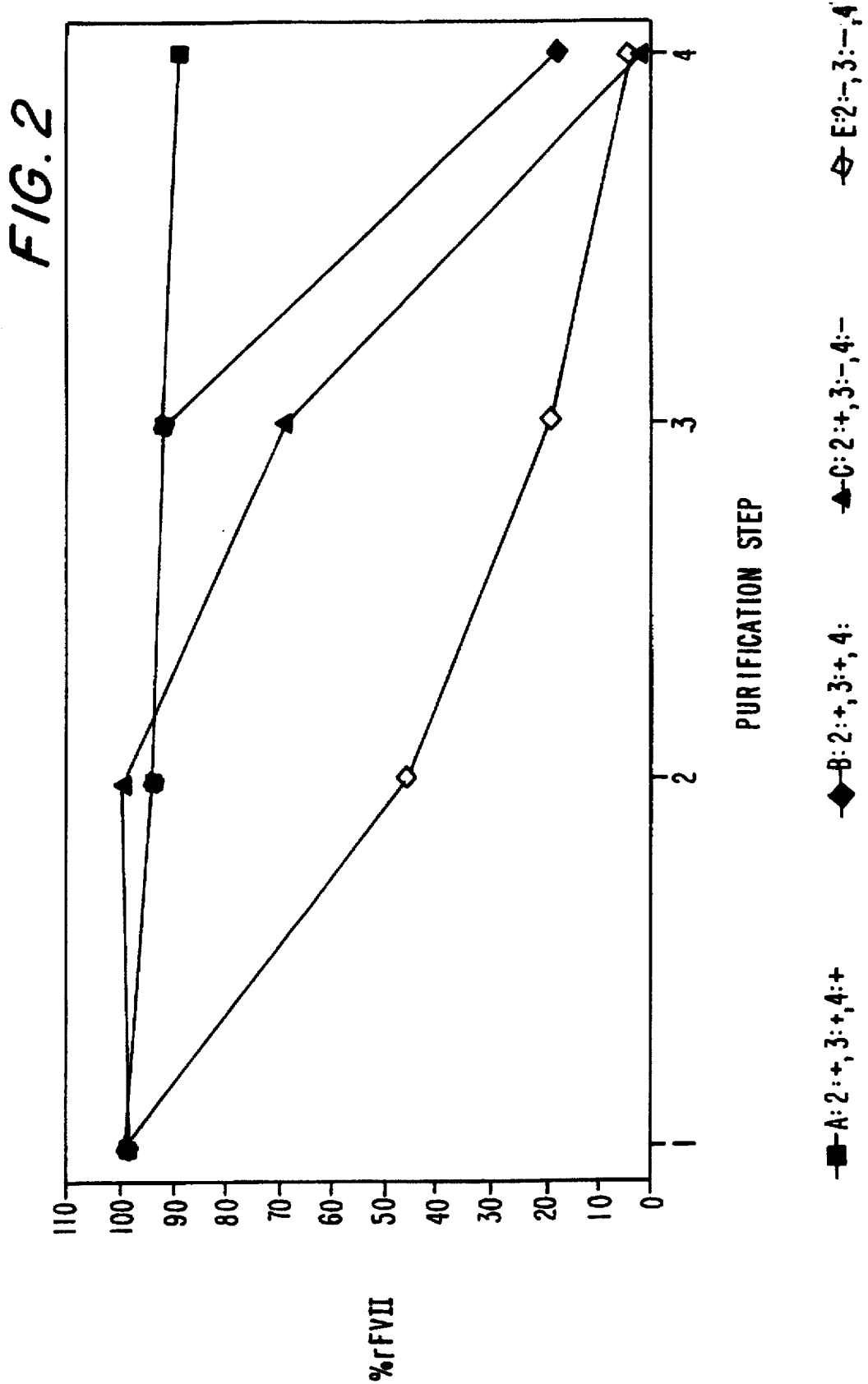

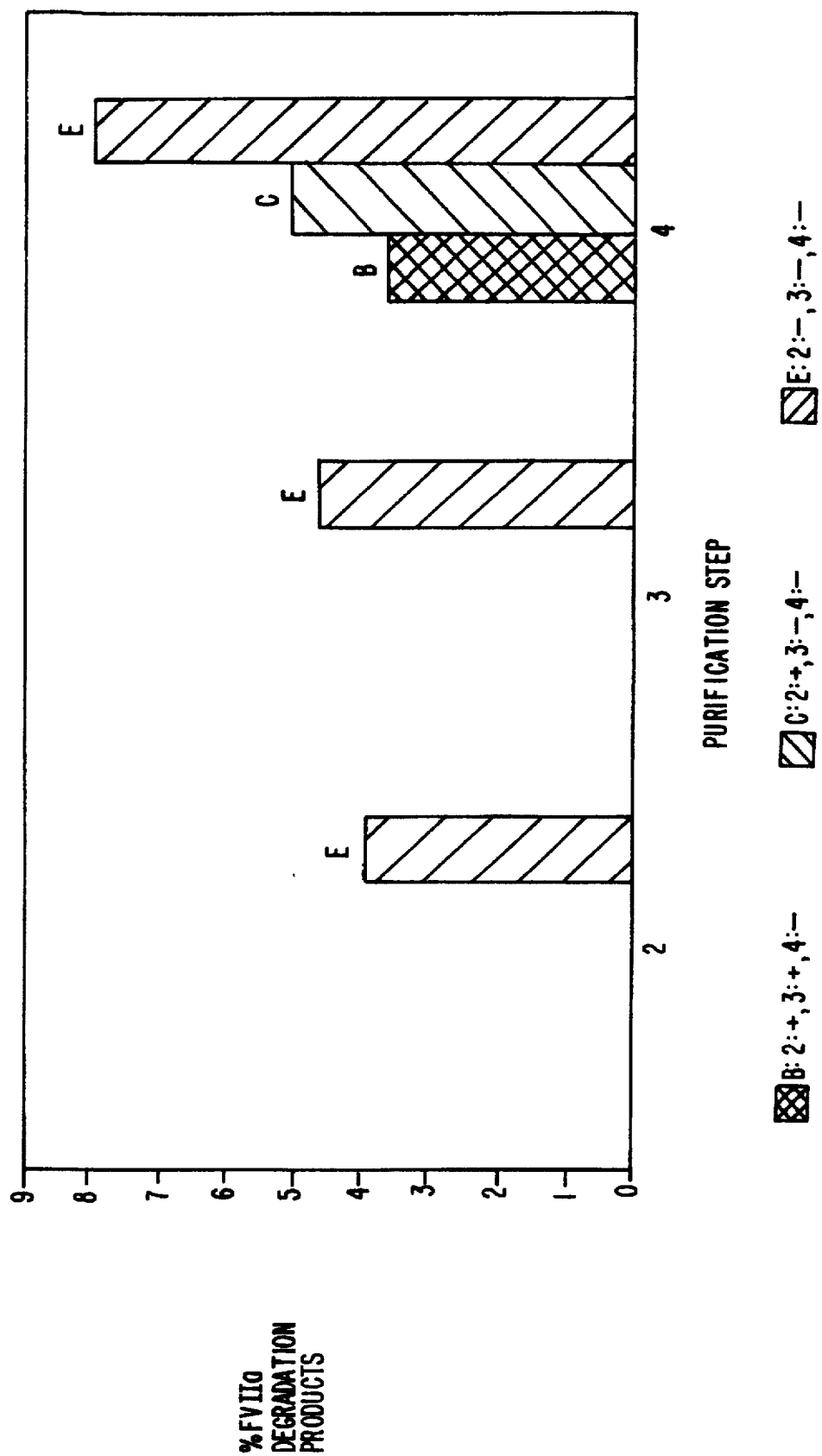

PURIFICATION OF FACTOR VII

CROSS-REFERENCE TO RELATED APPLICATIONS

This application is a 371 of PCT/DK94/00122 filed Mar. 24, 1994, published as WO94/22905 Oct. 13, 1994, which is incorporated herein by reference.

TECHNICAL FIELD

The present invention is related to a method for controlled activation and degradation of Factor VII.

BACKGROUND ART

Coagulation Factor VII (FVII) is a vitamin K dependent serine protease playing a key role in the extrinsic pathway of blood coagulation. It is synthesized in the liver and secreted into the blood where it circulates as a single-chain glycoprotein (zymogen) with a molecular weight of about 50,000. In its activated form, FVIIa, the protease catalyzes the activation of two other vitamin K dependent coagulation facors of the serine protease family, Factor IX (FIX) and Factor X (FX).

Activated FX (FXa) will then convert prothrombin into thrombin. Thrombin will then convert fibrinogen into fibrin, the major constituent of the clot.

Factor VII can be purified from plasma and activated into Factor VIIa by the methods described by Broze and Majerus, J.Biol.Chem. 255 (4) (1980) 1242–1247 and Hedner and Kisiel, J.Clin.Invest. 71 (1983) 1836–1841.

Factor VIIa may also be produced by recombinant DNA-technology by culturing in an appropriate medium mammalian cells transfected with a DNA-sequence encoding Factor VII, isolating the protein produced and activating said protein to Factor VIIa (European patent application No. 86302855.1).

Factor VIIa may be used in treating patients who have developed inhibitors to Factor VIII (Hedner, U. and Kisiel, W. J.Clin.Invest, 71 (1983) 1836–1841) and for the treatment of patients suffering from bleeding disorders such as platelet disorders including thrombocytopenia, von Willebrand's disease and others typically present in association with severe tissue damages (European patent application No. 86309197.1).

During purification of the plasma-derived bovine protein (Radcliffe & Nermerson, J.Biol.Chem. 250 (1975) 338–395) and the human recombinant protein (Thim et al., Biochemistry 27 (1988) 7785–7793), FVII was activated into the two-chain form by hydrolysis of the $Arg_{152}$-$Ile_{153}$ bond. The activation of FVII is greatly enhanced by adsorption on anion exchangers (diethylaminoethyl or trimethylaminoethyl modified polymeric gel matrices) (A. H. Pedersen et al., Biochemistry 28 (1989), 9331–9336). The mechanism by which the FVII activation is enhanced is not known. In addition to the activation, a fraction of the FVIIa molecules is cleaved primarily at positions 290 and/or 315 by autodegradation (E. M. Nicolaisen et al., FEBS Lett. 317 (1993) 245–249). Such degradation products are inactive molecules and their occurrence in the Factor VIIa preparation will lead to a lower specific activity of the final preparation. Furthermore, the amount and nature of the degradation products may vary from one production batch to another giving rise to preparations with a variable content of biologically active Factor VIIa. A content of degradation products in the final preparation may trigger the immune system of the patient. Readministration may then result in allergic reactions, which in severe cases may have a lethal course. Patients may also develop high titers of antibodies against Factor VIIa rendering subsequent treatment difficult or ineffective.

In order to prepare a purified FVIIa product with a low content of degradation products it is essential to control the activation and impede degradation during the purification process and subsequent processing. In contrast to FVIIa the single chain form, FVII, is resistant to or much less prone to cleavage in the heavy chain. It might therefore be an advantage to purify FVII in its single chain form.

It is therefore the purpose of the present invention to provide a purification process for FVII by which activation and degradation is avoided or kept at an acceptable low degree with the purpose of providing a homogeneous product of high purity which can then be activated into FVIIa in a further step in high yields to give a uniform and homogeneous product with high specific activity.

It is known that zinc ions inhibit the amidolytic and proteolytic activity of recombinant FVIIa (Pedersen, A. H. et al., Thrombosis and Haemostasis, 65 (1991 ), 528–534). It has now surprisingly been found that addition of zinc ions can be used to control the autoactivation of FVII and to impede the degradation of FVII/FVIIa during purification by means of chromatografic column materials.

DESCRIPTION OF THE INVENTION

In its broadest aspect the present invention is related to a method for controlled activation and degradation of FVII during purification whereby a solution of Factor VII is subjected to a number of chromatographic purification steps wherein $Zn^{++}$ is present at least in one of the purification steps.

In a more narrow aspect the present invention is related to a method for controlled activation and degradation of FVII wherein a solution of FVII is applied to a number of anion exchange and immune affinity columns.

In a preferred embodiment of the present invention the FVII solution is applied to the chromatographic columns in the following order: 1) anion exchange; 2) immune affinity; 3) anion exchange; 4) anion exchange column where $Zn^{++}$ is present in at least the first two steps.

BRIEF DESCRIPTION OF THE DRAWINGS

FIG. 1 illustrates the activation of FVII in the presence of anion exchange columns when varying the $Zn^{++}$ concentration.

FIG. 2 illustrates activation of rFVII to rFVIIa during purification schemes including $Zn^{++}$ in buffers in one or more of the purification steps.

The conditions for scheme A through E are given in table 1 and results are listed in table 2.

FIG. 3 illustrates FVIIa degradation during purification schemes including $Zn^{++}$ in buffers in one or more of the purification steps.

The conditions for scheme A through E are given in table 1 and results are listed in table 2.

Prior to setting forth the invention, it may be helpful to an understanding thereof to set forth definitions of certain terms to be used hereinafter:

FVII FVII will include FVII isolated from plasma or prepared by recombinant DNA-technology. It will also cover allelic variants that may exist and occur from one individual to another and FVII proteins being modified by amino acid residue deletions and/or substitutions which upon activation has the same or substantially the same biological activity for blood coagulation as endogenous human FVIIa.

"FVII" within the above definition will also cover FVII proteins with a variation in degree and location of glycosylation and/or other post-translational modifications depending on the chosen host cells and the cultivation conditions when expressed by recombinant DNA technology.

FVIIa biological activity: The FVIIa biological activity is characterized by the mediation of blood coagulation through the extrinsic pathway.

FVIIa activates FX to FXa, which in turn converts prothrombin to thrombin thereby initiating the formation of a fibrin clot.

Controlled activation and degradation: This expression will cover a process in which the activation and degradation of FVII during purification progress according to an intentional controlled variation of a given parameter (in this case the presence of $Zn^{++}$).

In absence of $Zn^{++}$, the purification process parameters have to be adjusted to the concomitant occurring activation and degradation reaction. In the presence of $Zn^{++}$ it has turned out to be possible to control these reactions making it possible to optimize purification and activation independently.

DETAILED DESCRIPTION

Human FVII will preferably be expressed in transfected mammalian Baby Hamster Kidney (BHK) cells as described in European patent application No. 86302855.1. The culture medium containing FVII and cell growth stimulating proteins will be separated from the cells by centrifugation and filtration prior to the chromatographic purification.

For the purpose of purification FVII will be adsorbed onto different types of chromatographic matrices such as: cat-ion exchangers, an-ion exchangers, immunoaffinity matrices, metal ion chelaters, dye-affinity matrices, hydrophobic interaction matrices and affinity matrices with immobilized biospecific ligands. The mechanism by which FVII adsorbs to the different matrices varies, hence the effect of $Zn^{++}$ on the activation of FVII might be different but still significant during adsorption to the different types of chromatographic matrices.

The zinc salt may be added to one or more of the eluate solutions and buffers used for equilibration and elution. The zinc salt may be any soluble zinc salt such as zinc acetate, zinc citrate, zinc chloride or zinc sulphate.

The $Zn^{++}$ concentration may vary between 10 µM and 1 mM and will preferably be between about 20 µM to about 1 mM, more preferably between about 40 µM to about 1 mM.

The subsequent activation of the purified FVII into FVIIa may be achieved using FXIIa as described by Hedner and Kiesel (J.Clin.Invest. 71 (1983), 1836–1841) or with other proteases having trypsin-like specificity (Kiesel and Fujikawa, Behring Inst. Mitt. 73 (1983), 29–42). Alternatively, FVII may be activated in the presence of polymeric macromolecules such as polylysine, matrix structures, substituted agarose gel or membranes.

EXPERIMENTAL PART

The purification scheme for purification and activation of rFVII to rFVIIa was performed through the following four successive chromatographic steps: step 1 anion exchange; step 2 immunoaffinity chromatography; step 3 anion exchange; step 4 anion exchange.

An experimental serial of purification schemes were conducted in which some of the schemes included addition of zinc salt to all the buffers of one or more of the chromatographic steps as outlined in Table 1.

Experimental conditions are given in example 2 to 4.

The reference experiment (E) was performed as example 2 except that no $Zn(CH_3\text{—}COO)_2$ was added.

TABLE 1

| Purification scheme | Chromatographic step | | | |
|---|---|---|---|---|
| | 1 | 2 | 3 | 4 |
| A | − | + | + | + |
| B | − | + | + | − |
| C | − | + | − | − |
| E (reference) | − | − | − | − |

+/− indicates the presence or absence of zinc salt in the buffers.

Each step eluate was assayed for the degree of FVII activation ( % FVII) and for the content of FVIIa degradation products. The conversion of FVII into the two chained FVIIa form was measured by standard polyacrylamide electrophoresis (PAGE) in sodiumdodecylsulfate (SDS) under reducing conditions combined with Coomassie Blue staining and quantification by laser densitometry.

The content of FVIIa degradation products was quantified by reverse phase high performance liquid chromatography (RP-HPLC) on a butyl bonded silica column in a linear acetonitrile gradient.

The results from experiments conducted essentially as described in the examples are listed in Table 2 and presented in FIG. 2 and FIG. 3. It is apparent from FIG. 2 that in presence of zinc ions (lines A, B and C) none or very limited rFVII activation took place during the immunoaffinty step (step 2) and the anion exchange steps (step 3 and step 4) (lines A and B).

In contrast hereto an extensive activation took place in step 2 (line E) and in step 3 and 4 (lines B, C and E) in absence of zinc ions.

It is also apparent that the interaction of zinc ions with FVII/FVIIa causing the inhibitory effect on the activation of FVII, is of an reversible nature; since after removal of the zinc ions, by complex binding with excess EDTA, FVII is activated during subsequent purification steps (lines B and C).

In step 1 apparently no activation took place in absence of zinc ions. This could be due to a much lower concentration of FVII on the column.

The step 1 eluat, which was used in all the experiments, contained less than 1% FVIIa.

TABLE 2

| Experiment | Purification steps | $Zn^{++}$ | % FVII (SDS-PAGE) | % FVIIa degraded (RP-HPLC) |
|---|---|---|---|---|
| A + B | 2 | + | 94 | 0 |
| | 3 | + | 92 | 0 |
| A | 4 | + | 89 | <2 |
| B | 4 | − | 18 | 3.6 |
| C | 2 | + | 99 | <2 |
| | 3 | − | 69 | <2 |
| | 4 | − | 2 | 5.0 |
| E | 2 | − | 46 | 3.9 |
| | 3 | − | 19 | 4.6 |
| | 4 | − | 4 | 8.0 |

EXAMPLE 1

Inhibition of the activation of FVII while bound to anion exchanger

The effect of $Zn^{++}$ on the activation of FVII was tested in an experiment in which purified FVII was adsorbed on Q-Sepharose FF matrix in presence of varying concentrations of $Zn^{++}$. 500 μg FVII was incubated with 50 μl Q-Sepharose FF in 800 μl buffer: 10 mM Tris, 50 mM NaCl, 2 mM $CaCl_2$ and varying concentrations of zinc acetate in 1.5 ml test tubes. After 1 hr and 2 hr the matrix was settled by centrifugation and the supernatant removed. 800 μl buffer 10 mM Tris, 50 mM NaCl, 25 mM $CaCl_2$ pH 8.0 was added and after mixing and centrifugation samples of the supernatant was withdrawn and analyzed for FVII/FVIIa by SDS-PAGE.

The results (FIG. 1) showed that in absence of $Zn^{++}$ 55% of the FVII was activated to FVIIa within 1 hr and more than 90% was activated after 2 hr.

In presence of 10 μM $Zn^{++}$ only 25% was activated after 1 hr. and only 73% was activated after 2 hr.

In presence of $Zn^{++}$ in concentrations above 40 μM there was no activation within 2 hr.

It is clear from this experiment that $Zn^{++}$ in the concentration range of about 10 μM to about 100 μM has an inhibitory effect on the activation of FVII in presence of anion exchangers and it is conceivable that $Zn^{++}$ has an effect on FVII activation at all concentrations of $Zn^{++}$ in the whole range from below 10 μM to 1 mM.

It appears that by varying the $Zn^{++}$ concentration it is possible to control the FVII activation rate constant and at high $Zn^{++}$ concentrations essentially "protect" FVII from activation and hence from degradation.

EXAMPLE 2

The purification and activation of rFVII to rFVIIa were performed through the following four chromatographic steps:

Step 1:

rFVII containing cell culture medium was adjusted to ion strength below 10 mS/cm by dilution and applied to a Q-Sepharose column pre-equilibrated with buffer A: 10 mM trihydroxymethylaminomethan (Tris); 150 mM NaCl pH 8.

After a washing step with 175 mM NaCl in the same buffer rFVII was eluted by buffer B: 10 mM Tris; 150 mM NaCl; 25 mM $CaCl_2$ pH 8.

Step 2:

The eluate solution containing 104 mg/l rFVII was adjusted to a final composition: 10 mM Tris; 1M NaCl; 25 mM $CaCl_2$; 70 μM $Zn(CH_3COO)_2$ pH 7.5 and applied to a Sepharose column with immobilized anti-FVII monoclonal antibody.

The antibody column was pre-equilibrated with buffer C: 10 mM Tris; 100 mM NaCl; 20 mM $CaCl_2$; 70 μM $Zn(CH_3COO)_2$ pH 7.5. The column was then washed with 10 mM Tris; 2M NaCl; 20 mM $CaCl_2$; 70 μM $Zn(CH_3COO)_2$ pH 7.5 followed by buffer C. Thereafter rFVII/rFVIIa was eluted by applying a buffer: 75 mM Tris; 30 mM trisodiumcitrate; 70 μM $Zn(CH_3COO)_2$ pH 7.5.

Step 3:

The eluate was immediatly applied to a Q-Sepharose column pre-equilibrated with buffer: 10 mM Tris; 150 mM NaCl; 70 μM $Zn(CH_3COO)_2$ pH 8.6.

The column was washed with the same buffer and rFVII/rFVIIa was eluted in a linear gradient from buffer A to buffer D: 10 mM Tris; 500 mM NaCl; 70 μM $Zn(CH_3COO)_2$ pH 8.6.

Step 4:

The fraction containing rFVII/rFVIIa was adjusted to an ion strength below 10 mS/cm by dilution and immediately applied to a Q-Sepharose column pre-equilibrated with buffer: 10 mM glycylglycine; 150 mM NaCl; 70 μM $Zn(CH_3COO)_2$ pH 8.6.

After washing with buffer: 10 mM glycylglycine; 175 mM NaCl; 70 μM $Zn(CH_3COO)_2$ pH 8.6; and buffer E: 10 mM glycylglycine; 100 mM NaCl; 70 μM $Zn(CH_3COO)_2$, pH 8.6, rFVII/rFVIIa was eluted in a linear gradient from buffer E to buffer: 10 mM -glycylglycine; 100 mM NaCl; 15 mM $CaCl_2$; 70 μM $Zn(CH_3COO)_2$, pH 8.6. The flow rate was 1 vol./hr.

The purified rFVIIa preparation had the following characteristics:

Content of rFVIIa: 345 mg/l measured by UV spectrosopy (OD280)

Content of foreign proteins <1% by RP-HPLC

Content of rFVII: 89% by SDS PAGE

Content of rFVIIa degradation products: <2 % by RP-HPLC

EXAMPLE 3

The purification and activation of rFVII to rFVIIa was performed through the following four chromatographic steps:

Step 1:

rFVII containing cell culture medium was adjusted to ion strength below 10 mS/cm by dilution and applied to a Q-Sepharose column pre-equilibrated with buffer A: 10 mM trihydroxymethylaminomethan (Tris); 150 mM NaCl pH 8.

After a washing step with 175 mM NaCl in the same buffer rFVII was eluted by buffer B: 10 mM Tris; 150 mM NaCl; 25 mM $CaCl_2$ pH 8.

Step 2:

The eluate solution containing 104 mg/l rFVII was adjusted to a final composition: 10 mM Tris; 1M NaCl; 25 mM $CaCl_2$; 70 μM $Zn(CH_3COO)_2$ pH 7.5 and applied to a Sepharose column with immobilized anti-FVII monoclonal antibody.

The antibody column was pre-equilibrated with buffer C: 10 mM Tris; 100 mM NaCl; 20 mM $CaCl_2$; 70 μM $Zn(CH_3COO)_2$ pH 7.5. The column was then washed with 10 mM Tris; 2M NaCl; 20 mM $CaCl_2$; 70 μM $Zn(CH_3COO)_2$ pH 7.5 followed by buffer C. Thereafter rFVII/rFVIIa was eluted by applying a buffer: 75 mM Tris; 30 mM trisodiumcitrate; 70 μM $Zn(CH_3COO)_2$ pH 7.5.

Step 3:

The eluate was immediatly applied to a Q-Sepharose column pre-equilibrated with buffer: 10 mM Tris; 150 mM NaCl; 70 μM $Zn(CH_3COO)_2$ pH 8.6.

The column was washed with the same buffer and rFVII/rFVIIa was eluted in a linear gradient from buffer A to buffer D: 10 mM Tris; 500 mM NaCl; 70 μM $Zn(CH_3COO)_2$ pH 8.6.

Step 4:

The fraction containing rFVII/rFVIIa was adjusted to 2 mM ethylenediaminetetraacetic acid (EDTA) and ion strength below 10 mS/cm by dilution and immidiatly applied to a Q-Sepharose column pre-equilibrated with buffer: 10 mM glycylglycine; 150 mM NaCl pH 8.6.

After washing with buffer: 10 mM glycylglycine; 175 mM NaCl pH 8.6. and buffer E: 10 mM glycylglycine; 100 mM NaCl pH 8.6, rFVII/rFVIIa was eluted in a linear gradient from buffer E to buffer: 10 mM glycylglycine; 100 mM NaCl; 15 mM CaCl$_2$ pH 8.6. The flow rate was 1 vol./hr.

The purified rFVIIa preparation had the following characteristics:

Content of rFVIIa: 492 mg/l measured by UV spectroscopy (OD280)

Content of foreign proteins <1% by RP-HPLC

Content of rFVII: 18% by SDS PAGE

Content of r FVIIa degradation products: 3.6% by RP-HPLC

EXAMPLE 4

The purification and activation of rFVII to rFVIIa was performed through the following four chromatographic steps.

Step 1:

rFVII containing cell culture medium was adjusted to ion strength below 10 mS/cm by dilution and applied to a Q-Sepharose column pre-equilibrated with buffer A: 10 mM trihydroxymethylaminomethan (Tris); 150 mM NaCl pH 8.

After a washing step with 175 mM NaCl in the same buffer rFVII is eluted by buffer B: 10 mM Tris; 150 mM NaCl; 25 mM CaCl$_2$ pH 8.

Step 2:

The eluate solution containing 104 mg/l rFVII was adjusted to a final composition: 10 mM Tris; 1M NaCl; 25 mM CaCl$_2$; 70 μM Zn(CH$_3$COO)$_2$ pH 7.5 and applied to a Sepharose column with immobilized anti-FVII monoclonal antibody.

The antibody column was pre equilibrated with buffer C: 10 mM Tris; 100 mM NaCl; 20 mM CaCl$_2$; 70 μM Zn(CH$_3$COO)$_2$ pH 7.5. The column was then washed with 10 mM Tris; 2M NaCl; 20 mM CaCl$_2$; 70 μM Zn(CH$_3$COO)$_2$ pH 7.5 followed by buffer C.

Thereafter rFVII/rFVIIa was eluted by applying a buffer: 75 mM Tris; 30 mM trisodiumcitrate; 70 μM Zn(CH$_3$COO)$_2$ pH 7.5.

Step 3:

The eluate was adjusted to 2 mM EDTA and immediately applied to a Q-Sepharose column pre-equilibrated with buffer: 10 mM Tris; 150 mM NaCl pH 8.6.

The column was washed with the same buffer and rFVII/rFVIIa was eluted in a linear gradient from buffer A to buffer D: 10 mM Tris; 500 mM NaCl pH 8.6.

Step 4:

The fraction containing rFVII/rFVIIa was adjusted to ion strength below 10 mS/cm by dilution and immediately applied to a Q-Sepharose column pre-equilibrated with buffer: 10 mM glycylglycine; 150 mM NaCl pH 8.6.

After washing with buffer: 10 mM glycylglycine; 175 mM NaCl pH 8.6. and buffer E: 10 mM glycylglycine; 100 mM NaCl pH 8.6, rFVII/rFVIIa was eluted in a linear gradient from buffer E to buffer: 10 mM glycylglycine; 100 mM NaCl; 15 mM CaCl$_2$ pH 8.6. The flow rate was 1 vol./hr.

The purified rFVIIa preparation had the following characteristics:

Content of rFVIIa: 1.2 mg/ml measured by UV spectroscopy (OD280)

Content of foreign proteins <1% by RP-HPLC

Content of rFVII: 1% by SDS-PAGE

Content of rFVIIa degradation products: 6.7% by RP-HPLC

We claim:

1. A process for controlled activation and controlled degradation of Factor VII during purification of Factor VII whereby a solution of Factor VII is subjected to a number of chromatographic purification steps wherein $Zn^{++}$ is present in at least one of the purification steps.

2. A process according to claim 1, wherein a solution of Factor VII is applied to one or more anion exchange and one or more immunoaffinity chromatography columns.

3. A process according to claim 1, wherein $Zn^{++}$ is present in the form of a soluble zinc salt.

4. A process according to claim 1, wherein $Zn^{++}$ is present in a concentration of from about 10 μM to about 1 mM.

5. A process according to claim 4, wherein $Zn^{++}$ is present in a concentration of from about 20 μM to about 1 mM.

6. A process according to claim 4, wherein $Zn^{++}$ is present in a concentration of from about 40 μM to about 1 mM.

7. A process according to claim 2, wherein the FVII solution is applied to the chromatographic columns in the following order: 1) anion exchange; 2) immunoaffinity; 3) anion exchange; 4) anion exchange and wherein $Zn^{++}$ is present in at least two steps.

* * * * *